(12) United States Patent
Duncan

(10) Patent No.: US 6,479,277 B2
(45) Date of Patent: *Nov. 12, 2002

(54) METHOD AND APPARATUS FOR DISRUPTION OF BIOLOGICAL MATERIAL

(75) Inventor: Kelvin Winston Duncan, Christchurch (NZ)

(73) Assignee: Cellular Improvements Ltd., Christchurch (NZ)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/424,962

(22) PCT Filed: Jun. 4, 1998

(86) PCT No.: PCT/NZ98/00072

§ 371 (c)(1),
(2), (4) Date: Nov. 30, 1999

(87) PCT Pub. No.: WO98/54987

PCT Pub. Date: Dec. 10, 1998

(65) Prior Publication Data

US 2002/0127701 A1 Sep. 12, 2002

(30) Foreign Application Priority Data

Jun. 4, 1997 (NZ) .............................................. 328013
Sep. 15, 1997 (NZ) .............................................. 328740

(51) Int. Cl.$^7$ .............................................. C12M 1/00
(52) U.S. Cl. .............................. 435/283.1; 435/286.6; 422/243; 422/255; 241/2
(58) Field of Search ...................... 426/447; 435/306.1, 435/283.1, 284.1, 286.6; 422/243, 255; 241/2

(56) References Cited

U.S. PATENT DOCUMENTS

| 4,084,757 A | 4/1978 | Rakitin et al. ............... 241/301 |
| 4,310,554 A | * 1/1982 | Olson et al. ................... 426/40 |
| 4,746,071 A | 5/1988 | Grunhoff et al. ............... 241/2 |
| 5,288,619 A | * 2/1994 | Brown et al. ................ 435/134 |
| 5,306,637 A | 4/1994 | Lin et al. ..................... 435/259 |

FOREIGN PATENT DOCUMENTS

| EP | 319439 | 6/1989 |
| WO | W.O. 9215669 | 9/1992 |
| WO | WO 97/05787 | 2/1997 |
| WO | W.O. 97 09992 | 3/1997 |

OTHER PUBLICATIONS

Dekker, Robert F.H. "The Utilization of Autohydrolysis–Exploded Hardwood (*Eucalyptus regnans*) and Softwood (*Pinus radiata*) Sawdust for the Production of Cellulolytic Enzymes and Fermentable Substrates", Biocatalysis, 1987 vol. 1, pp. 63–75.

Puri, V.P. and Mamers, H. "Explosive Pretreatment of Lignocellulosic Residues with High–Pressure Carbon Dioxide for the Production of Fermentation Substrates", Biotechnology and Bioengineering. vol. XXV, (1983) pp. 3149–3161.

* cited by examiner

*Primary Examiner*—David A. Redding
(74) *Attorney, Agent, or Firm*—Greer, Burns & Crain, Ltd.

(57) ABSTRACT

A method of disrupting biological material includes drying particulate material, mixing the material with a gas under pressure, releasing the pressure explosively and collecting the resultant product. The biological starting material is any particulate material and includes: cells with membranes, cells with rigid cell walls, non-cellular biological material, intra-cellular material, and unbounded homogenous material. Apparatus for batch, semi-continuous and continuous operation of the method is provided. Included is a chamber with at least one inlet valve and at least one outlet valve and collection means. The chamber is capable of withstanding at least 800 bar, preferably 30 bar pressure. The particle size of the starting material is in the range 0.1 to 2000 μm and of the resultant product, less than 2 μm.

13 Claims, 7 Drawing Sheets

METHOD AND APPARATUS FOR DISRUPTION OF BIOLOGICAL MATERIAL

TECHNICAL FIELD

The present invention relates to apparatus for the explosive decompression of biological material, and to a method of explosive decompression of biological material. More specifically, the apparatus and method relate to the explosive decompression of biological material resulting in a product that is homogenous in size.

BACKGROUND ART

Various methods of disrupting cell walls of biological material are known, the method (and associated apparatus) depending on whether the cell walls are rigid, elastic, neither, or do not exist. For example, sonic disruption of cells is used on non-rigid materials. However this is not effective on cells with rigid cell walls.

Mechanical methods for disrupting cells of biological material, such as grinding or milling, are also used. However, such methods have two possible disadvantages. Firstly, hot spots can develop in the material being ground or the temperature of the material increases. If proteins or enzymes are the desired product from the biological material, such heat (whether general or localised) can seriously degrade or render the desired products inactive. Secondly, on some cells, particularly botanical cells with very strong cell walls, this method does not always rupture the cell wall.

Methods using the application of a magnetic or electromagnetic field to the cells are also capable of disrupting cell walls. However this method is not always commercially reliable or versatile.

A further, known method of cellular disruption is that as discussed in WO 97/05787 (Ashourian). This publication discloses the use of an homogeniser to homogenize fruit cells within a puree or fluid or to produce same to reduce the size of cell components under pressure. However, the disruption is disclosed as producing a puree or an homogenised fluid. The process appears to be inapplicable to intra-cellular disruption of particulate material.

In all the above methods of cell wall disruption the result is a rip or tear in the cell wall. This is not always a break or disruption of sufficient size to release the contents of the cell for easy access to the cytoplasm and intact nucleus and organelles. Further, the above methods do not result in an homogenous mixture.

An object of the present invention is the provision of apparatus and a method for the production of a mixture containing disrupted biological material. A further object of the invention is the provision of such apparatus and method which overcome the disadvantages of known methods of disruption of biological material as described above, with reference to cells with rigid cell walls or non-rigid and non-elastic cell walls.

DISCLOSURE OF INVENTION

For the purposes of this specification "biological material" includes but is not limited to: cells with cell membranes, cells with rigid cell walls, cells with non-elastic, non-rigid cell walls, non-cellular biological material, intra-cellular material, unbounded homogenous material, and a combination thereof; all material being biological material that is, or can be, rendered particulate in appearance.

The present invention provides a method of disrupting biological material, said method including the steps of:

drying particulate biological material;

mixing said particulate material with a gas at a pressure between 4 and 800 bar and allowing said mixing to continue until gas penetration of some or all of the particulate material is effected;

releasing the pressure explosively and reducing the pressure of the particulate material to atmospheric at a temperature of not more than 400° C.;

collecting the resultant product.

The present invention further provides a method of disrupting biological material, said method including:

drying particulate biological material;

mixing said particulate material with a gas at a pressure between 4 and 800 bar and allowing said mixing to continue until gas penetration of some or all of the particulate material is effected, wherein said particulate material is mixed in small portions;

separating a small portion of mixed material and gas and releasing the pressure explosively and reducing the pressure within the small portion of the particulate material to atmospheric at a temperature of not more than 400° C.;

collecting the resultant product; and repeating the above three steps, said repetition being in the nature of a continuous process.

Preferably the above methods produce a homogenous mixture of pieces and cytoplasm. Preferably the methods further include, after the step of releasing the pressure explosively, the step of allowing the explosively decompressed material to impact on or along a shear cone or wall.

Preferably the pressure is in the range 4 and 30 bar pressure.

Preferably the gas is selected from the group consisting of: air, carbon dioxide, nitrogen, helium, hydrogen, argon, neon, helium; and a combination of these. The selection of the gas used is dependent on the material to be processed, as the gas needs to be substantially inert with reference to that material. The selection is also dependent on commercial availability and cost of the gas(es). Preferably the time period for release of the pressure is less than one second, and more preferably 0.1 second.

Preferably, the gas penetration of the particulate material has reached an equilibrium before the pressure is explosively released. In the instance of particulate material with cell walls, this equilibrium occurs when the gas is in equilibrium within the cell wall. This time is generally between 1 to 10 minutes. However, more time may be used for this step of the method. Optionally the time for this step is between 1 and 3 minutes.

Preferably the particulate material is initially of a size between 0.1 to 2000 $\mu$m, more preferably 0.1 to 50 $\mu$m, and most preferably 0.1 to 20 $\mu$m. With this range of particle sizes it can be seen that particles the size of bacteria, viruses, procaryotic, eucaryotic cells and cellular inclusions can be the biological material.

The biological material can be selected from the group including: material with rigid cell walls, cells with non-elastic, non-rigid cell walls, cells with cellular membranes, non-cellular biological material. Examples of such material include pollens, spirulina and other rigid cell walled unicellular species. The biological material can be biological material with non-rigid cell walls at room temperature which walls become rigid walls or non-elastic, non-rigid walls under extremely low temperatures. Examples of intracellular material or non-cellular material include organelles and nuclei, and shark cartilage. An example of such material with cell membranes is green lipped mussel powder.

The temperature range in which the above methods can be performed is −200° to 400° C., more preferably −196° to 40° C., and most preferably −15° to 30° C.

Optionally said methods produce a resultant product with a reduced count of biological contaminants, as compared with that of the starting particulate material, when the starting material is non-fungal material. The method optionally further includes the step of treating the resultant product with ultra-violet light.

Optionally, when the starting material is fungal, said methods produce a resultant product with an increased cell-forming count.

The present invention further provides apparatus for the disruption of biological material (as hereinbefore defined), said apparatus including:
a chamber with a first inlet means for particulate material and a second inlet means for gases and an outlet means for gases and material, said chamber being capable of withstanding pressures up to 800 bar; and
collection means attached to said outlet means;
wherein said outlet means includes a valve which is capable of releasing the pressure within the chamber in one second or less.

The present invention further provides apparatus for the disruption of biological material (as hereinbefore defined); said apparatus including:
a chamber with a first inlet means for particulate material and a second inlet means for gases and an outlet means for gases and material, said chamber being capable of withstanding pressures up to 800 bar;
collection means attached to said outlet means; wherein
said inlet means for particulate material includes two valves (an inner and an outer valve), each independently operated by an actuator, said valves being separated by an inlet chamber which is capable of withstanding pressures of up to 800 bar;
said outlet means for gases and material includes two valves (an inner and an outer) each independently operated by an actuator, said valves being separated by an outlet chamber which is capable of withstanding pressures of up to 800 bar;
wherein the outlet valve of the outlet means is capable of releasing the pressure within the outlet chamber in one second or less.

The present invention further provides apparatus for the disruption of biological material (as hereinbefore defined), said apparatus including:
a chamber with a first inlet means for particulate material and a second inlet means for gases and an outlet means for gases and material, said chamber being capable of withstanding pressures up to 800 bar;
collection means attached to said outlet means; wherein
said inlet means for particulate material includes one valve operated by an actuator;
said outlet means for gases and material includes two valves (an inner and an outer) each independently operated by an actuator, said valves being separated by an outlet chamber which is capable of withstanding pressures of up to 800 bar;
wherein the outlet valve of the outlet means is capable of releasing the pressure within the outlet chamber in one second or less.

Preferably said apparatus operates to produce a homogenous mixture of cell wall pieces and cytoplasm.

Preferably said apparatus also includes means to vibrate said chamber to facilitate the mixing of the particulate material and the gas. The collection means may be any known means of collecting fine particles, for example: a cyclone dust collector, a dust bag, an electrostatic dust precipitator and a combination of these. Preferably the collection means collects the exploded material under inert or substantially inert conditions.

Preferably the collection means further includes a cone placed within the collection means adjacent the outlet from the outlet valve of the outlet chamber; the position of the cone being such that the particulate material is still travelling at considerable speed, as a result of the explosive decompression, when the material impacts the cone and slides into the collection means.

Preferably, any of the embodiments of the apparatus operate in the pressure range 4 to 30 bar pressure.

Optionally, any of the embodiments of the apparatus can be operated under axenic conditions. Optionally the above-described apparatus can operated at temperatures in the range −200° to 400° C. more preferably −196° to 40° C. and most preferably −15° to 30° C.

BRIEF DESCRIPTION OF THE DRAWINGS

By way of example only, preferred embodiments of the present invention are described in detail with reference to the examples and to the accompanying drawings, in which.

BEST MODES FOR CARRYING OUT THE INVENTION

Figure 1:
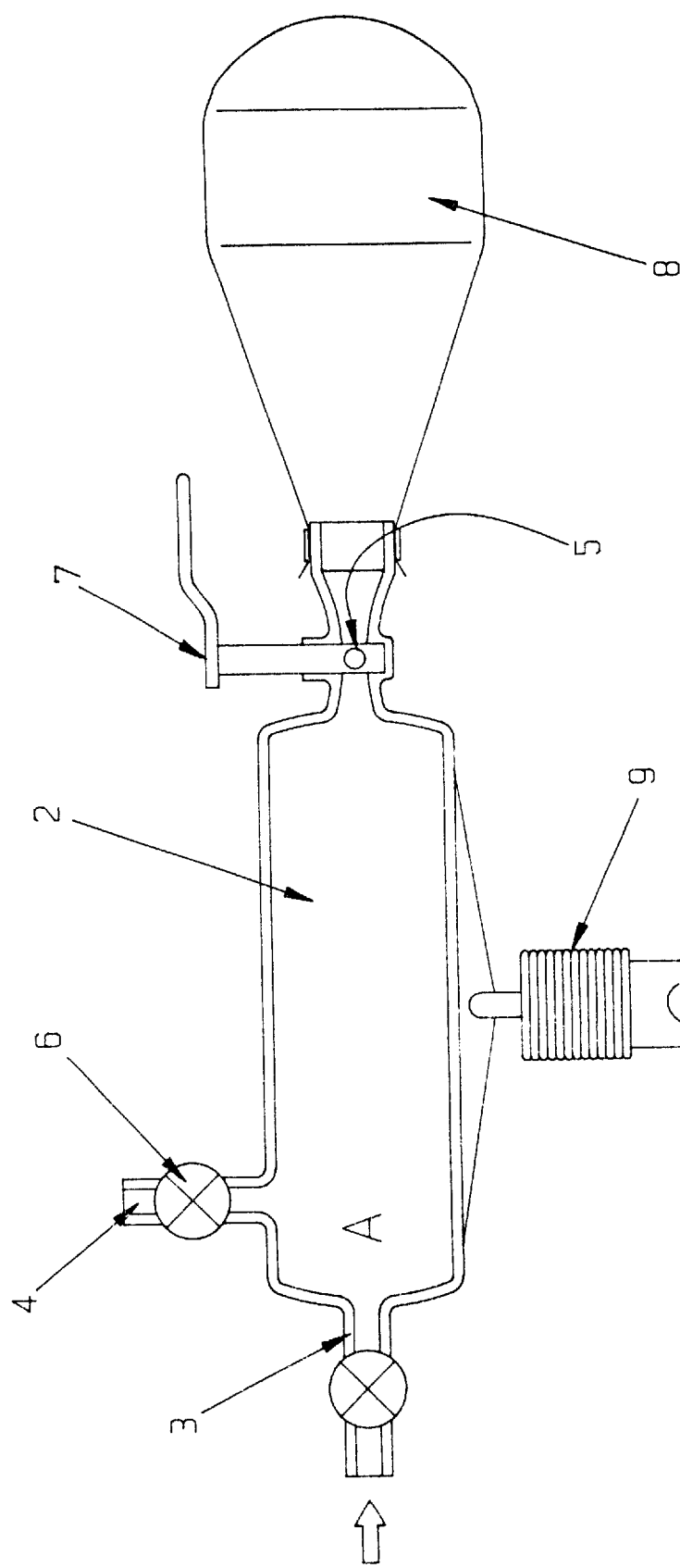
FIG. 1 is a diagrammatic representation of a first preferred embodiment of the apparatus of the present invention for batch operation of the method of the present invention.

Referring to FIG. 1, a chamber 2 is there shown, with a gas inlet pipe 3, a powder entry pipe 4 and an outlet pipe 5. The chamber 2 is approximately cylindrical and capable of withstanding pressures in excess of 30 bar.

The gas inlet pipe 3 is connected by known means to a gas cylinder (not shown) with known cutoff valving. The gas cylinder may alternatively be any other source of pressurised gas. The gas is any gas which is inert to the powder to be disrupted. Examples of such gases, which are commercially available at a reasonable cost are: air, nitrogen and carbon dioxide. However, if so desired, another gas may be used. Examples of such gases include: the noble gases and hydrogen. A combination of gases may be used, if so desired.

The powder inlet pipe 4 includes a valve 6 capable of withstanding the pressures used in the chamber 2. The outlet pipe 5 includes a rapid discharge valve 7 of known type (for example, a ball valve) which can withstand the pressures in the chamber 2 and which can open extremely rapidly, so that the contents of the chamber 2 can be evacuated in under 1 second. In practice it has been found that this time is preferably 0.75 second or less.

The outlet pipe 5 is connectable to a collector 8, which can be any known type of powder collector into which expanding gases can pass quickly. Examples of such collectors include a dust bag, a cyclone collector, an electrostatic precipitator, and a combination of these.

The chamber 2 is cylindrical is shape and is preferably of a diameter less than 150 millimeters. If so desired, an appropriate, larger pressure vessel could be used. The chamber 2 can rest on a vibrator 9, of known type, if so desired. Such vibrator 9 can be electrically or mechanically driven. The vibrator 9 may be replaced by another mechanical equivalent, for example springs, if so desired.

The above described apparatus is used as follows: powder enters the chamber 2 through the powder inlet pipe 4, and the inlet valve 6 is closed. The rapid discharge valve 7 is closed. Gas is introduced into the chamber 2 through the gas inlet pipe 3. The gas valving is closed when the pressure in the chamber 2 is at 30 (or at the pre-determined pressure) bar. The vibrator 9 operates to keep the gas and the powder mixing in the closed chamber 2.

After a mixing period of between 20 seconds to 10 minutes, the rapid discharge valve 7 is opened. The powder and gas exit the chamber 2 in an explosive decompression from the chamber 2. The powder remnants are collected in the collector 8. The mixing period is sufficient for the gas to penetrate some or all of the particulate material. If, for example, the particulate material has cell walls, the mixing period is sufficient for the gas to penetrate the cell walls and reach an equilibrium pressure there. If so desired, the mixing period may be longer, or shorter.

In practice it has been found that at 10 bar pressure, one kilogram of material can be efficiently mixed with nitrogen gas in one minute.

The rapid discharge valve 7 preferably permits the explosive removal of the gas and powder from the chamber 2 in less than one second. More preferably the time is between 0.75 and 0.1 seconds. In the first preferred embodiment of the method, the explosive decompression is carried out at a room temperature or not more than 40° C. If the release of organelles, proteins or enzymes from the cells is desired, then the use of temperatures any greater than this may lead to degradation of the desired product.

Preferably the collection of the powder remnants in the collector 8 is under inert or substantially inert conditions. Optionally this is achieved by expelling substantially all the air from the collector 8 prior to the opening of the rapid discharge valve 7, and collecting the powder remnants in the presence of some or all of the expelled gas from the chamber 2. Alternatively, the collector 8 may be operated with a gaseous atmosphere of pure nitrogen or other inert gas; or operate in a strong vacuum until the rapid discharge valve 7 is opened.

The above described chamber 2 and collector 8 have been described with reference to FIG. 1, which displays the chamber 2 and collector 8 in a horizontal position. If so desired, the orientation of the chamber 2, collector 8 and associated parts can be vertically oriented.

The powder used includes any of the biological materials as previously defined. Examples of such materials include, but are not limited to: plant cells with rigid walls (for example, cells with a skeletal function, and spores or pollens); animal cells with fibroid or calcified cell membranes or matrices; and bacterial cells.

EXAMPLES

In the examples below the material was dried and ground to a fine powder, if not already in that form, to produce the starting material. The method used was a batch operation at less than 30 bar pressure and at a room temperature between 15° to 30° C. The starting material and the resultant product were photographed under the same conditions.

Example 1

Figure 6A:
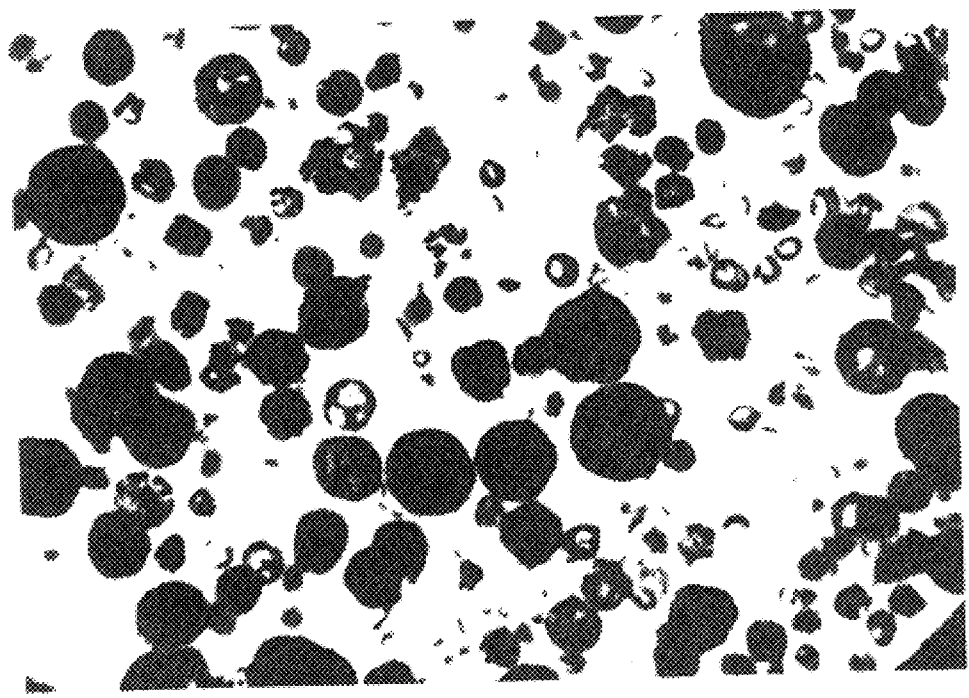
FIG. 6 shows a photograph of spirulina at a magnification of 200 times, taken before (a) and after (b) the operation of the method on the material in the second preferred embodiment of the apparatus of the present invention.
Figure 6B:
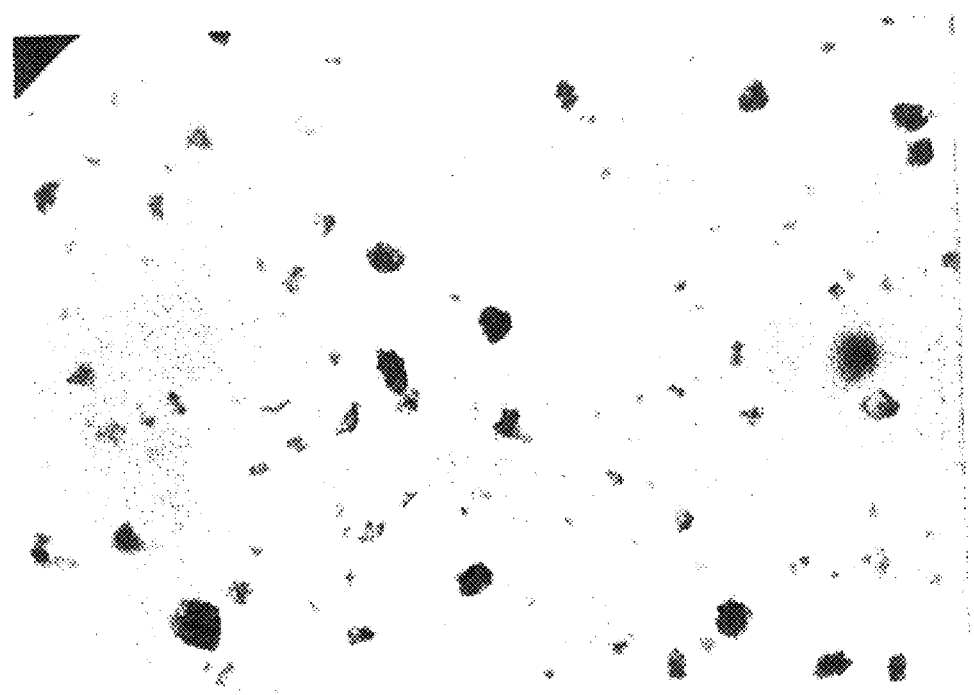

An example is Spirulina (known as either Spirulina (Arthrospira) platensis or Arthrospira (Spirulina) platensis ("spirulina")). This is commonly seen in two species—A (s) platensis and A (s) maxima. FIG. 6a shows powdered spirulina (200 times magnification) which was used as the starting material. FIG. 6b is the resultant product at the same magnification.

Example 2

Figure 4A:
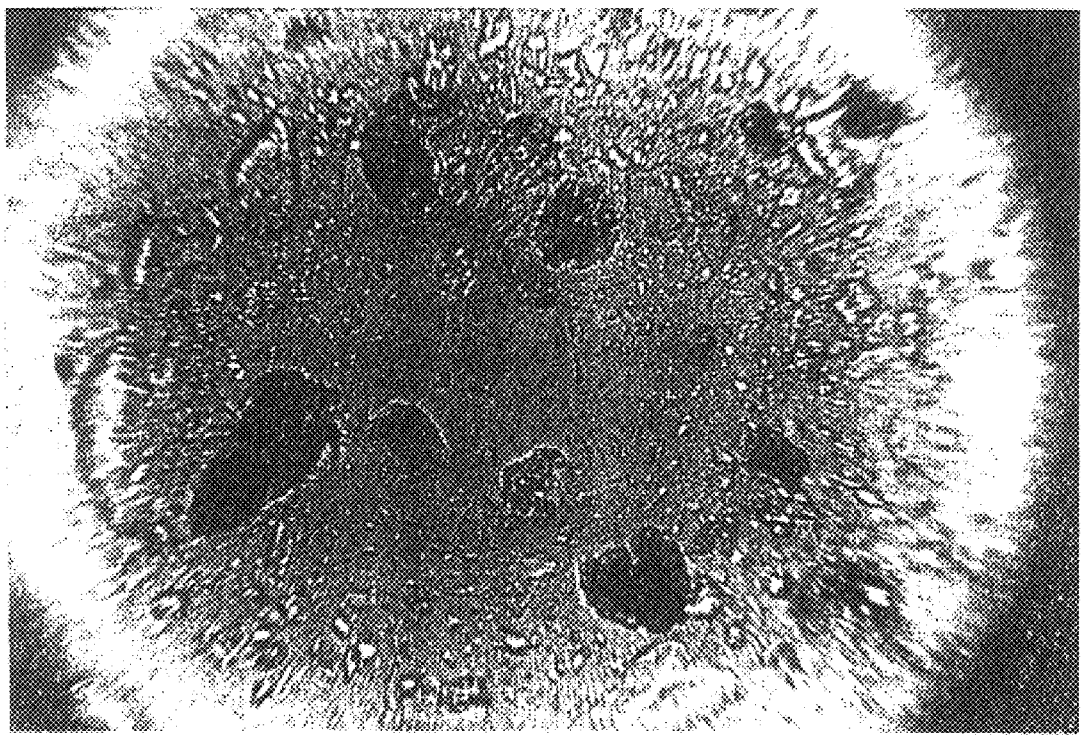
FIG. 4 shows a photograph of shark cartilage at a magnification of 100 times, taken before (a) and after (b) the operation of the method on the material in the second preferred embodiment of the apparatus of the present invention.
Figure 4B:
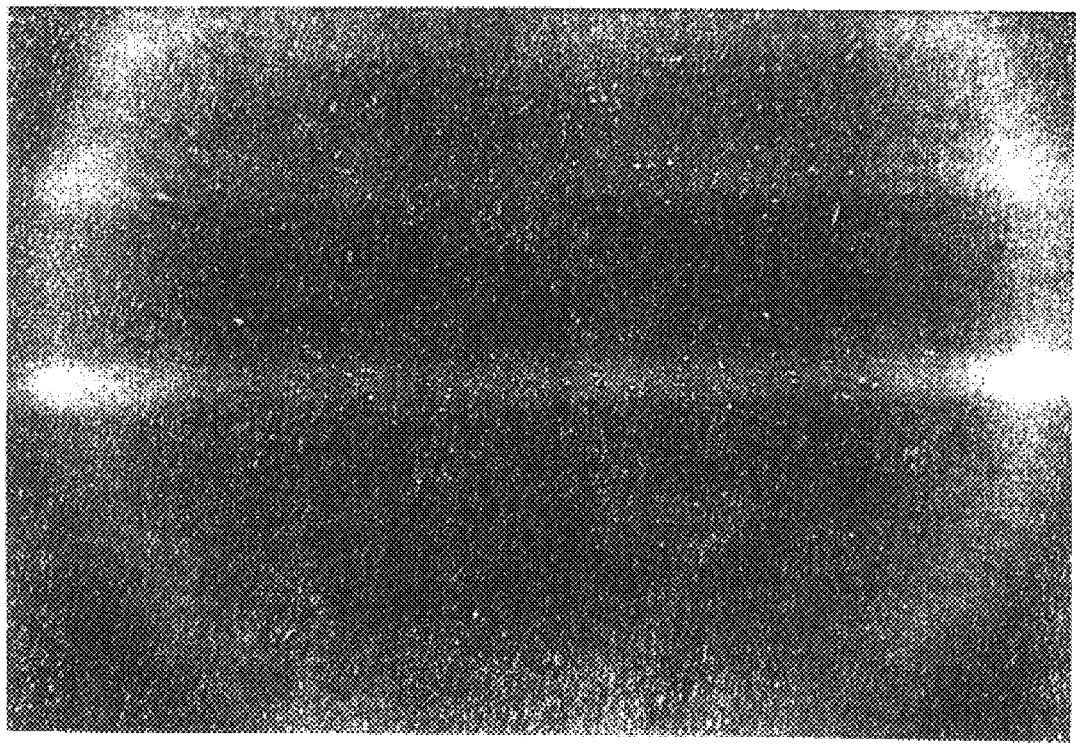

Referring to FIGS. 4a and 4b, the starting material and the resultant product, where the material was shark cartilage is there shown. The cartilage shown in FIG. 4a was previously milled to a 'super fine' level by a known milling machine.

Example 3

Figure 5:
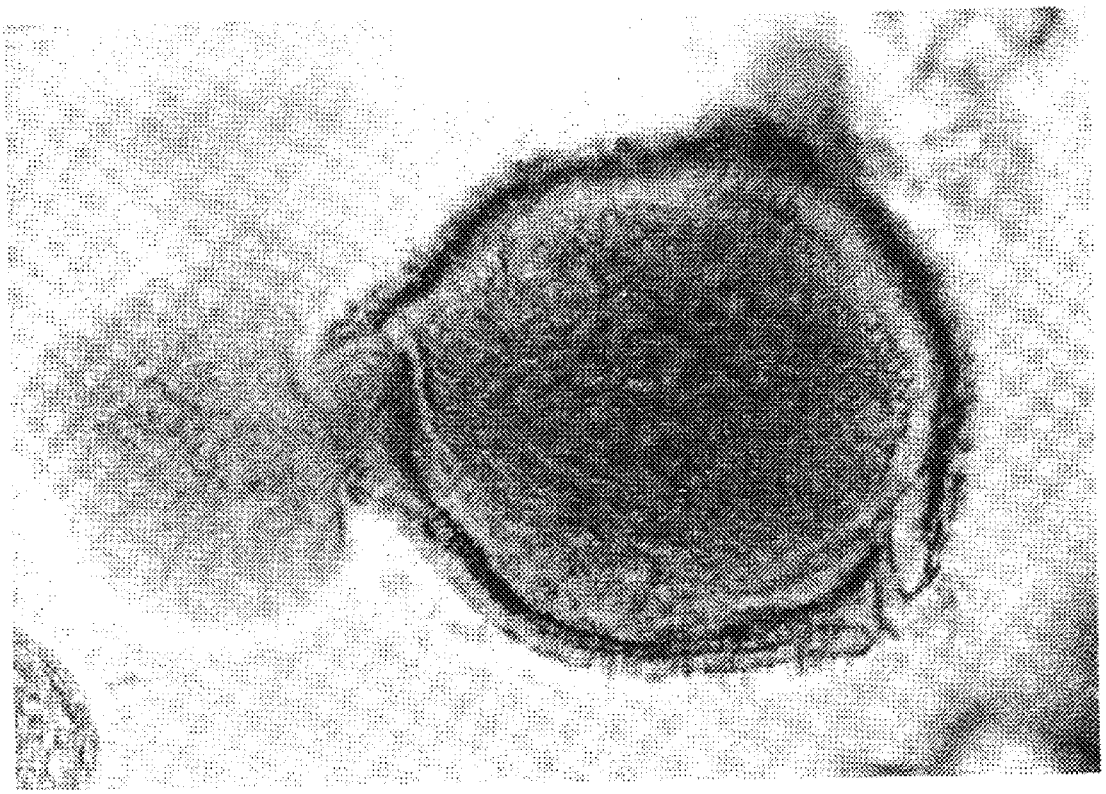
FIG. 5 shows a photograph of a pollen grain at a magnification of 500 times, taken after the operation of the method on the material in the second preferred embodiment of the apparatus of the present invention.

FIG. 5 shows a pollen grain immediately after explosive decompression. The grain is magnified 500 times. The cell wall has been breached in three places (one of which is under the top edge of the grain). Cytoplasm has been discharged through the breaches.

Example 4

Figure 7A:
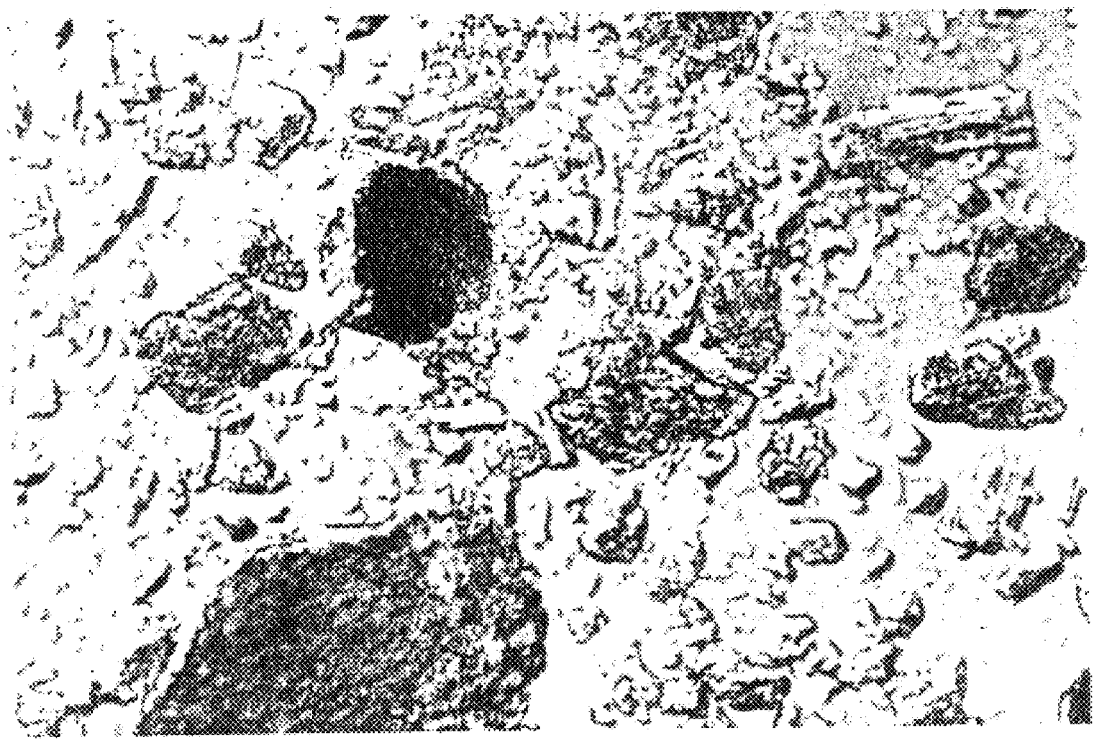
FIG. 7 shows a photograph of green lipped mussel powder at a magnification of 10 times, taken before (a) and after (b) the operation of the method on the material in the second preferred embodiment of the apparatus of the present invention.
Figure 7B:
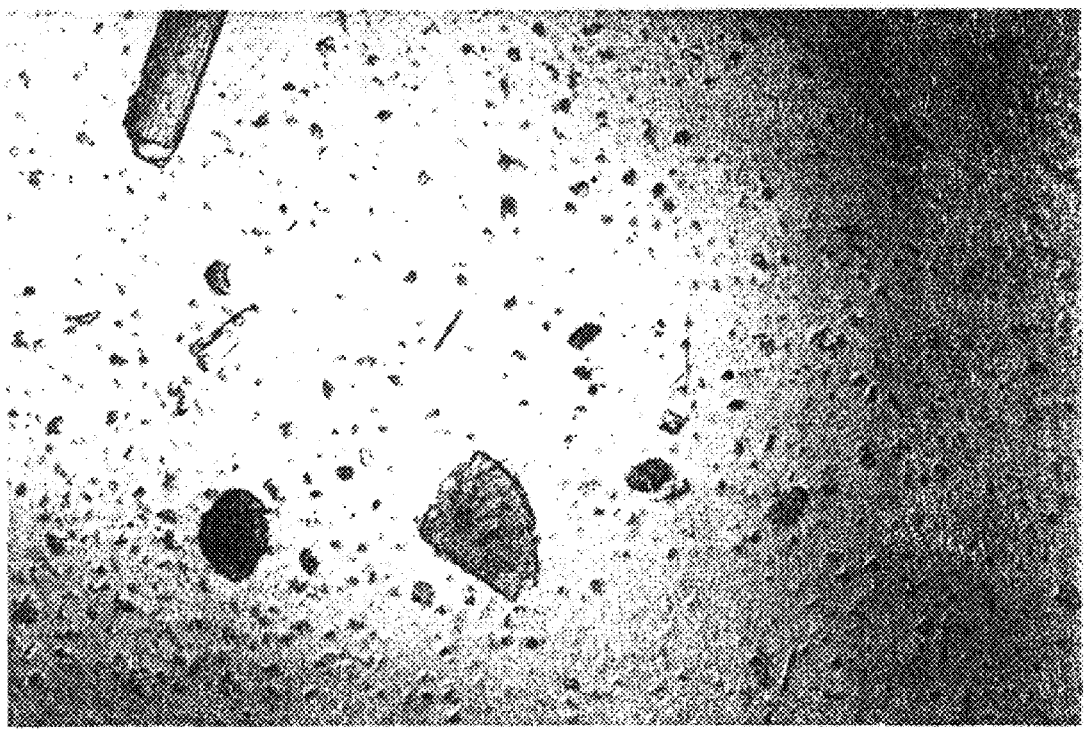

FIG. 7 shows two views (before (a) and after (b)) where the starting material is green lipped mussel powder. The magnification is 10 times. The powder is produced by drying the mussel, and shredding or milling to produce a fine powder. FIG. 7b shows the resultant product from the powder of FIG. 7a.

The material used in these examples: spirulina, pollen, shark cartilage and green lipped mussel are all commercially available products.

There are cells, or other biological material, that do not contain a rigid cell wall or a cell wall that is non-rigid but also non-elastic. This occurs at normal room or operating temperatures for such cells. Such cell walls, for some material, can be rendered rigid or non-rigid but also non-elastic, by decreasing the temperature of the material to a temperature in the range −15° to −200°. This can be achieved by lowering the temperature of the chamber 2 and collector 8 and by reducing the temperature of the biological material prior to passing it though the chamber 2.

In practice it has been found that with one kg of dried particulate spirulina, the degree of cell wall disruption at varying pressure is as follows:

| | |
|---|---|
| 4 bar: | 40% |
| 7 bar: | 65% |
| 10 bar: | 90–95% |

These results are based on a mixing time of 2 minutes and a release time for the rapid discharge valve of 0.75 seconds. It has been found in practice that this method reduces the average particle size from about 20 $\mu$m to 1–2 $\mu$m.

In practice it has been found that, when the particulate material is cellular in nature, this method and apparatus disrupts only the cell walls . The nucleus and other organelles are left intact, but accessible by standard chemical and biochemical reactions. In practice it has also been found that cell walls are substantially uniformly disrupted, so that the resultant cell wall particles are in a narrow range of particle sizes. If the nuclei and organelles are dried out these can then be disrupted by a further passing of the material through the chamber 2.

If so desired, the gas used could also be collected after use and recycled after appropriate filtering.

The above described method and apparatus have been described with reference to a batch operation. However it will be appreciated that the method could also be used in a continuous or semi-continuous process (using a reciprocating pump for the pressure variation differential required), without departing from the scope of the invention. Similarly, the same method could be used again on material already passed through the batch operation, either in the same equipment, or in a series of chambers 2.

Figure 2:
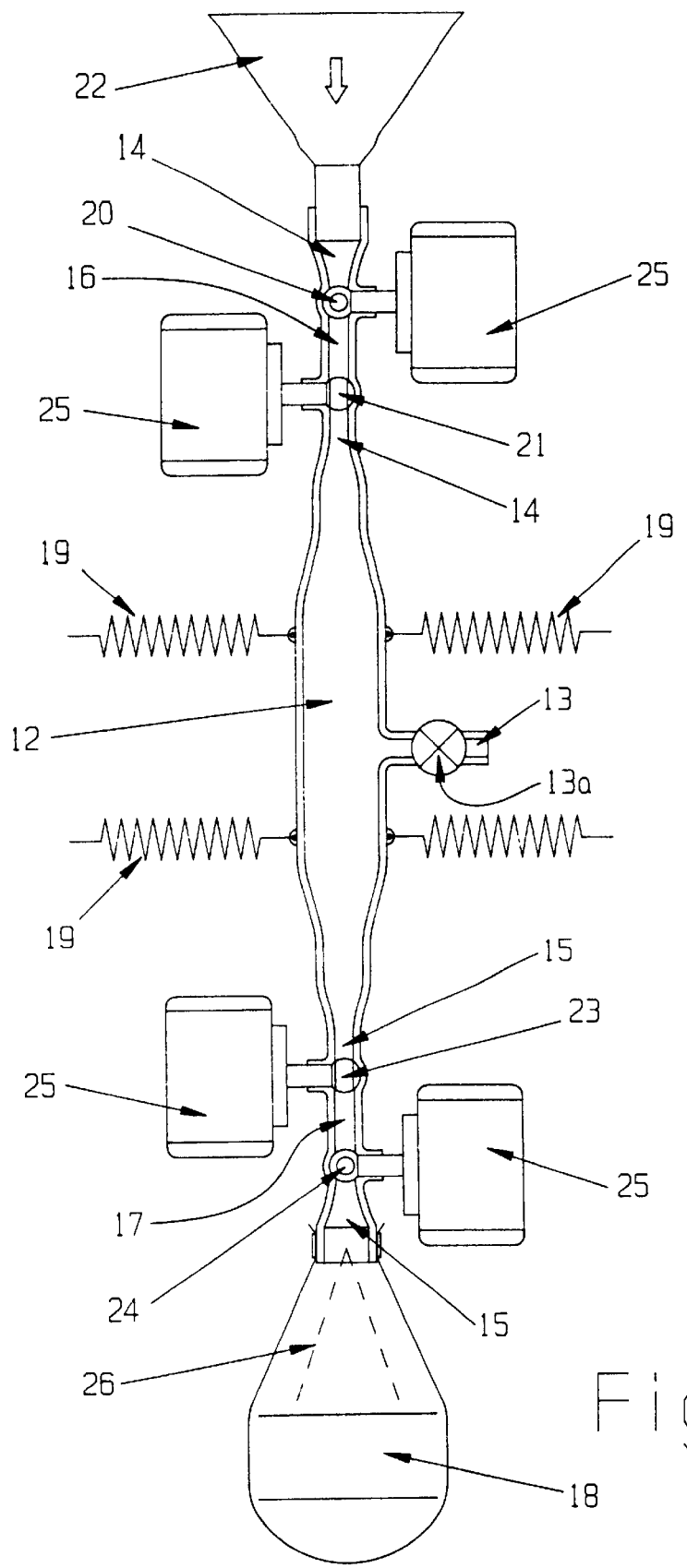
FIG. 2 is a diagrammatic representation of apparatus of a second preferred embodiment of the present invention for continuous operation of the method of the present invention.

Referring to FIG. 2, a second preferred embodiment of the apparatus of the present invention, for a continuous process operation, is thereshown. Said apparatus includes a chamber 12, a gas inlet pipe 13, a powder entry pipe 14 and an outlet pipe 15. The chamber 12 is approximately cylindrical and capable of withstanding pressures in excess of 30 bar.

The gas inlet pipe 13 is connected by known means to a gas cylinder (not shown) with known cutoff valving. The gas cylinder may alternatively be any other source of pressurised gas. The gas is any gas which is inert to the powder to be disrupted, as described above with reference to the first preferred embodiment of the invention.

The entry pipe 14 includes an inlet chamber 16 which has a capacity of less than 5 mL, preferably 3 mL. The inlet chamber 16 is capable of withstanding the same pressures as the chamber 12. At each end of the inlet chamber 16 is a valve. The valve connecting the inlet chamber 16 to the chamber 12 is the inner inlet valve 21. The valve connecting the inlet chamber 16 to a hopper 22 is the outer inlet valve 20. The valves 20, 21 are capable of withstanding the pressures used within the chamber 12, 16; for example, ball valves.

The outlet pipe 15 includes an outlet chamber 17 which has a similar volume and pressure capacity to that of the inlet chamber 16. At each end of the outlet chamber 17 is a valve. The valve connecting the outlet chamber 17 to the chamber 12 is the inner outlet valve 23. The valve connecting the outlet chamber 17 to a collector 18 is the outlet outer valve 24. The valves 23, 24 are capable of withstanding the pressures used within the chambers 12, 17; for example ball valves. Additionally, the outer outlet valve 24 is a rapid discharge valve which can be opened extremely rapidly, so that the contents of the outlet chamber 17 can be evacuated to atmospheric pressure in under 1 second. In practice it has been found that this time is preferably 0.75 seconds or less.

The hopper 22 is releasably connected to the upper or outer end of the gas entry pipe 14 and releasably sealed thereto. The hopper 22 is of known design for containing particulate material. If so desired, the hopper 22 may include a vibrator or other known means for the prevention of ridging of material within the hopper 22.

The outlet pipe 15 is connectable to the collector 18, which can be any known type of powder collector though which expanding gases can pass quickly. Examples of such collectors include a dust bag, a cyclone collector, an electrostatic precipitator, and a combination of these. The collector 18 may further include, positioned within the collector 18, a shear wall or shear cone 26. The tip of the shear cone 26 is adjacent the exit of the outer outlet valve 24, with the shear cone 26 being aligned to the same axis as the chamber 12.

The valves (20, 21, 23, 24) are each controlled by an actuator 25 of known type. Preferably, each actuator 25 is operated pneumatically and capable of remote computer control. With the positioning of an appropriate level sensor (not shown) in the hopper 22 and on the gas inlet pipe 13, the apparatus can be remotely monitored and controlled electronically. Each actuator 25 also includes a means to manually override any automated operation.

The chamber 12 is cylindrical in shape and is preferably of a diameter less than 150 mm. If so desired, an appropriate, larger pressure vessel could be used. The chamber 12 is shown in FIG. 2 with a vertical axis, but is capable of operation at any angle. The chamber 12 can be vibrated or shaken. If such assistance to mixing within the chamber 12 is required, this can be achieved by appropriate operation of four springs 19 attached to the external wall of the chamber 12. The second end of each of the springs 19 can be attached in known manner to a framework (not shown). The chamber 12 can then be shaken or vibrated in known manner. If so desired, other mechanical equivalents to the springs 19 may replace the springs 19, as described above with reference to the first preferred embodiment.

The above described apparatus works as follows: all valves (20, 21, 23, 24) are closed and the chamber 12 brought up to the operating pressure by use of the gas from inlet pipe 13. The attendant valve 13a is closed so that the chamber 12 is at the normal operating pressure, (for example 16 bar). Preferably this is between 10 and 20 bar, depending on the material to be ruptured but can be up to 800 bar pressure.

The dry powder to be disrupted is placed in the hopper 22. The outer inlet valve 20 is opened. Any excess gas under pressure is released through the powder, stirring the powder. Alternatively, if so desired, tubing or piping arrangements (not shown) may be used adjacent the outer inlet valve 20 as a bypass to vent all or most of the expelled gas away from the powder.

A quantity of powder falls (under gravity, or is pushed) into the inlet chamber 16. The outer inlet valve 20 is closed and the inner inlet valve 21 opened. The powder enters the chamber 12 and the inner inlet valve 21 is closed. This operation of the valves 20, 21 continues in a cyclical process, each cycle taking approximately 3 seconds. This time may be varied, to more or less, as is desired. The variation will depend on the required average residence time required for the particulate material in the chamber 12.

The outlet valves (23, 24) also operate a similar cycle. The inner outlet valve 23 opens, allowing approximately 3 mL of material and gas under pressure to enter the outlet chamber 17. The inner outlet valve 23 is closed and the outer outlet valve 24 is opened, with the material and gas being explosively decompressed into the collector 18. The time for explosive decompression is less than one second, and preferably between 0.1 and 0.75 seconds. Once all gas and material is vented, the outer outlet valve 24 is closed and the cycle is repeated.

In practice it has been found appropriate for the chamber 12 to have an internal volume of approximate 750 mL (being 600 mm long and having a diameter of approximately 50 mm). With approximately 3 mL of particulate material entering and leaving the chamber 12 every three seconds, the approximate time of residence of material within the chamber 12 is two to three minutes. However with appropriate variation of the cycles of the inlet and outlet valves (20, 21, 23, 24) this residence time can be varied between 20 seconds to 10 or more minutes.

For example, the minimum average residence time for a particulate material with a cell wall or membrane required is the time taken to achieve an equilibrium pressure of the gas in the cell wall or membrane. The chamber 12 is capable of operating at approximately room temperature.

Any variations in the internal pressure of the chamber 12 can be monitored by known means and the gas inlet valve 13a operated to allow more gas to enter the chamber 12, to maintain as close to a constant pressure within the chamber 12, as possible.

The powder remnants, after leaving the outer outlet valve 24, impact on the shear cone 26. This action aids in tearing apart or shattering the ruptured pieces of the material. This assists in obtaining uniformity of the piece size in the disruption of the cell walls and leads to a small, consistent range of ruptured particle sizes within the ruptured material.

The manner of collection of the powder remnants is as previously described. Also, as previously described, the chamber 12 can be vibrated (using the springs 19) to assist the attaining of a gas pressure equilibrium within the cell walls of the particulate material in the chamber 12.

The above described apparatus can be seen to operate a continuous cycle. With the size of chamber 12, as given above, and the described duty cycle of the two sets of valves (20, 21, 23, 24), between 5 to 10 kilograms of particulate material can be processed per hour. With a residence time within the chamber 12 of less than two minutes or a larger chamber (etc), the quantity of material processed may be varied to suit particular requirements.

As with the first preferred embodiment the gas can be recycled, if so desired.

Whist the above described apparatus is used for a continuous operation, it will be appreciated that batch operations are also possible, without departing from the scope of the invention.

Figure 3:
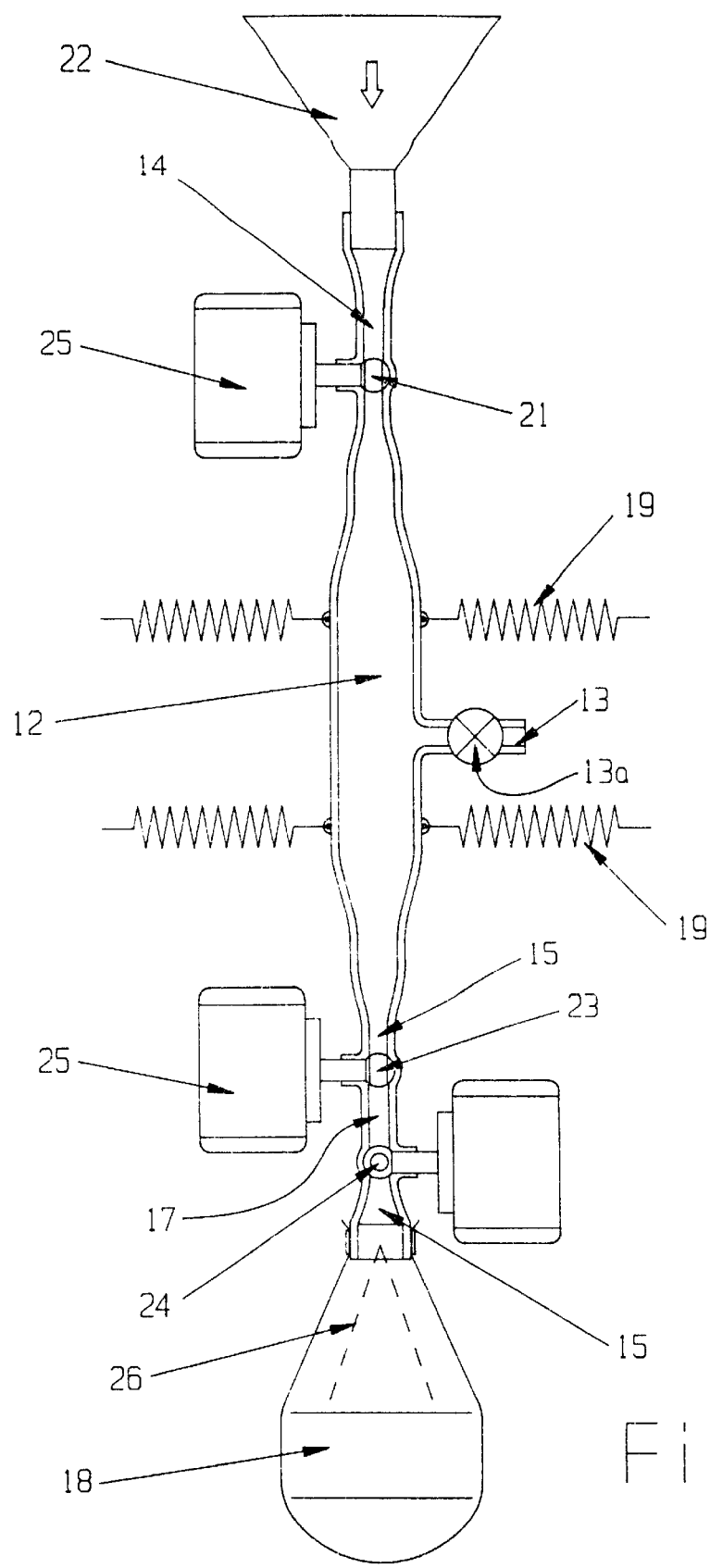
FIG. 3 is a diagrammatic representation of apparatus of a third preferred embodiment of the present invention for semi-continuous operation of the method of the present invention.

Referring to FIG. 3 a third preferred embodiment of the apparatus of the present invention is thereshown. Unless otherwise specified, like numbers refer to like parts of the second preferred embodiment of the apparatus. The major difference between the second and third embodiments is that the inlet chamber (16) and the outer inlet valve 20 are absent. This results in a different, semi-continuous cycle.

The apparatus of the third preferred embodiment operates as follows: the valves 13a, 21, 23 are closed so that the chamber 12 is isolated. The particulate material is placed in the hopper 22. The inlet valve 21 is opened and the material allowed to enter the chamber 12. When approximately 600 mL of material have entered the chamber the inlet valve 21 is closed.

The gas inlet valve 13a is opened and the chamber 12 is pressurised to the pre-determined required pressure (as described previously above). The material is left in the chamber 12 for a minimum of between 1 to 10 minutes, preferably 2 minutes. If so desired, the material may remain in the chamber 12 for longer than is the minimum required.

The outlet chamber 17 and outlet valves 23, 24 them operate in the same manner as is described for the second preferred embodiment. The one difference is that the outlet chamber 17 is larger in size, being in the range 3 to 10 mL in size.

The cycle is repeated until all the material in the chamber 12 is emptied through the outlet chamber 17. The entire process described is then repeated. As is desired, new material may be added to the hopper 22 for each cycle, or material may remain within the hopper 22 during each cycle.

Within this semi-continuous process, given the dimensions above for the chamber and the residency time, each cycle takes approximately 6 to 10 minutes. Thus, with a material having a specific gravity of 0.5 it is possible to process up to 3 kg per hour of material.

Optionally, and if so desired, any of the preferred embodiments described or referred to herein incorporate the encasing of the chamber (2, 12) in an impact-resistant plastic (not shown) of known type.

The operation of the first preferred embodiment at lowered temperatures can also be achieved for the second and third embodiments by lowering the temperature of the chamber 12 and collector 18 and by reducing the temperature of the biological material prior to passing it though the chamber 12. The temperature ranges of the first preferred embodiment can be applied in the second and third embodiments.

The apparatus of any embodiment is capable of being operated under axenic conditions. It has been found that, with the selection of appropriate starting biological material, the resultant product may have a reduced contamination count as compared with the count for the dried particulate starting material. However the biological material needs to be non-fungal material.

With all the preferred embodiments of the present invention as described or incorporated herein, it will be appreciated that the apparatus may include means to ground or earth all the component parts of the apparatus for the avoidance of static build-up and to remove the potential for a dust explosion.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

What is claimed is:

1. An apparatus for disrupting dried particulate biological material, said apparatus comprising:
    a chamber with a first inlet means for said material and a second inlet means for gases and an outlet means for gases and material, said chamber being capable of withstanding pressures up to 800 bar;
    collection means attached to said outlet means;
    said outlet means for gases and material includes an inner valve and an outer valve, each said valve independently operated by an actuator, said valves being separated by an outlet chamber which is capable of withstanding pressures of up to 800 bar; and
    said outer valve is capable of releasing the pressure within the outlet chamber in one second or less.

2. An apparatus for disrupting dried particulate biological material, said apparatus comprising:

a chamber with a first inlet means for said material and a second inlet means for gases and an outlet means for gases and material, said chamber being capable of withstanding pressures up to 800 bar; and collection means attached to said outlet means;

said outlet means includes at least one outlet valve, which is capable of releasing the pressure within the chamber in one second or less; and said first inlet means includes an inner inlet valve and an outer inlet valve, each independently operated by an actuator, said inlet valves being separated by an inlet chamber which is capable of withstanding pressures of up to 800 bar.

3. The apparatus as claimed in claim 2 wherein said outlet means for gases and material includes an inner outlet valve and an other outlet valve each independently operated by an actuator, said outlet valves being separated by an outlet chamber which is capable of withstanding pressures of up to 800 bar.

4. The apparatus as claimed in claim 1 wherein said apparatus further includes a shear cone or wall immediately adjacent said outlet means.

5. The apparatus as claimed in claim 2 wherein said apparatus further includes a shear cone or wall immediately adjacent said outlet means.

6. The apparatus as claimed in claim 1 wherein said material is selected from the group consisting of: cells with cell membranes, cells with rigid cell walls, cells with non-elastic cell walls, cells with non-rigid cell walls, non-cellular biological material, intra-cellular material, unbounded homogenous material, shredded biological material and a combination thereof.

7. The apparatus as claimed in claim 2 wherein said material is selected from the group consisting of: cells with cell membranes, cells with rigid cell walls, cells with non-elastic cell walls, cells with non-rigid cell walls, non-cellular biological material, intra-cellular material, unbounded homogenous material, shredded biological material and a combination thereof.

8. The apparatus as claimed in claim 7 wherein said cells with rigid cell walls include pollens and spirulina.

9. The apparatus as claimed in claim 7 wherein said cells with rigid cell walls include pollens and spirulina.

10. The apparatus as claimed in claim 1 wherein said apparatus is operated under conditions selected from the group consisting of: axenic conditions, inert conditions, and a combination thereof.

11. The apparatus as claimed in claim 2 wherein said apparatus is operated under conditions selected from the group consisting of: axenic conditions, inert conditions, and a combination thereof.

12. The apparatus as claimed in claim 1 wherein the collection means is selected from the group consisting of; a filter, a cyclone dust collector, a dust bag, an electrostatic dust precipitator and a combination thereof.

13. Apparatus as claimed in claim 2 wherein the collection means is selected from the group consisting of: a filter, a cyclone dust collector, a dust bag, an electrostatic dust precipitator and a combination thereof.

* * * * *